United States Patent [19]

Doersen et al.

[11] Patent Number: 5,286,643

[45] Date of Patent: Feb. 15, 1994

[54] RAT OSTEOSARCOMA CELL LINE OSR-8

[75] Inventors: Claus-Jens W. Doersen; Robert J. Isfort, both of Cincinnati, Ohio

[73] Assignee: The Procter & Gamble Company, Cincinnati, Ohio

[21] Appl. No.: 903,431

[22] Filed: Jun. 24, 1992

[51] Int. Cl.$^5$ .......................... C12N 5/06; C12P 21/02
[52] U.S. Cl. ............................... 435/240.2; 435/70.1; 435/240.1; 530/350
[58] Field of Search ................... 435/240.1, 240.2, 7.1; 530/350

[56] References Cited

U.S. PATENT DOCUMENTS 5,035,901  7/1991  Anderson et al. .................. 424/573

FOREIGN PATENT DOCUMENTS 0350641    1/1990  European Pat. Off. ...... A61K 37/02
2164042    3/1986  United Kingdom ........ A61K 37/00
WO91/18620 12/1991 World Int. Prop. O. ... A61K 37/02
WO91/18622 12/1991 World Int. Prop. O. ... A61K 37/36

OTHER PUBLICATIONS

Majeska et al., 1980, Endocrinology, vol. 107, pp. 1494-1503, "Parathyroid Hormone-Responsive Clonal Cells . . . ".

Miller et al., 1990, Cancer Research, vol. 50, pp. 7950-7954, "Frequency and Structure of p53 Rearrangements . . . ".

Huang et al., 1988, Science, vol. 242, pp. 1563-1566, "Suppression of the Neoplastic Phenotype by Replacement . . . ".

Ikeda et al., 1989, Jpn. J. Cancer Res., vol. 80, pp. 6-9 "Amplification of Both c-myc and c-raf-1 Oncogenes . . . ".

Amitani et al., 1975, Gann, vol. 66, pp. 327-329 "Osteogenic Induction by Cell-Free Material . . . ".

Chandar, N., B. Billig, J. McMaster and J. Novak, "Inactivation of p53 Gene in Human and Murine Osteosarcoma Cells", British Journal of Cancer, (Feb. 1992), vol. 65, No. 2, pp. 208-214.

Masuda, H., C. Miller, H. P. Koeffler, H. Battifora and M. J. Cline, "Rearrangement of the p53 Gene in Human Osteogenic Sarcomas", Proc. Natl. Acad. Sci., (Nov. 1987), vol. 84, pp. 7716-7719.

Rodan, G. A. and M. Noda, "Gene Expression in Osteoblastic Cells", Critical Review Eukaryotic Gene. Expression, (1991), vol. 1, Issue 2, pp. 85-91.

Rodan, G. A., J. K. Heath, K. Yoon, M. Noda and S. B. Rodan, "Diversity of the Osteoblastic Phenotype", Cell and Molecular Biology of Vertebrate Hard Tissues, (1988), Ciba Foundation Symposium 136, pp. 78-91.

Smith, H. S., "In Vitro Properties of Epithelial Cell Lines Established From Human Carcinomas and Nonmalignant Tissue", J. Natl. Cancer Inst., (Feb. 1979), vol. 62, No. 2, pp. 225-230.

(List continued on next page.)

Primary Examiner—Robert J. Hill, Jr.
Assistant Examiner—Sally P. Teng
Attorney, Agent, or Firm—Brahm J. Corstanje; Milton B. Graff, IV; David L. Suter

[57] ABSTRACT

The present invention relates to a novel cell line isolated from a rat osteosarcoma wherein the cell line has the following characteristics: a) a normal p53 gene; b) a normal RB-1 gene; c) a normal c-myc gene; d) a normal c-fos gene; e) a deregulated immediate early gene response; f) a canalicular network MATRIGEL ™ growth pattern; g) poorly tumorigenic in congenitally athymic mice; h) no alkaline phosphatase activity; i) an ability to produce one or more of the following growth factors: 1) a non-heparin binding growth factor, 2) a first heparin binding growth factor, 3) a second heparin binding growth factor, and 4) a third heparin binding growth factor; and j) an ability to be serially propagated greater than sixty population doublings.

The present invention also relates to growth factors having the characteristics of growth factors isolated from the rat osteosarcoma cell line.

The present invention further relates to a process for producing such growth factors comprising growing the cells of the present invention in a culture medium and recovering the growth factors.

1 Claim, 3 Drawing Sheets

OTHER PUBLICATIONS

Sturm, S. A., P. G. Strauss, S. Adolph, H. Hameister and V. Erfle, "Amplification and Rearrangement of c-myc in Radiation-induced Murine Osteosarcomas", Cancer Research, (Jul. 1990), vol. 50, pp. 4146–4153.

Vukicevic, S., F. P. Luyten, H. K. Kleinman and A. H. Reddi, "Differentiation of Canalicular Cell Processes in Bone Cells by Basement Membrane Matrix Components: Regulation by Discrete Domains of Laminin", Cell, (Oct. 1990), vol. 63, pp. 437–445.

Wozney, J. M., V. Rosen, A. J. Celeste, L. M. Mitsock, M. J. Whitters, R. W. Kirz, R. M. Hewick and E. A. Wang, "Novel Regulators of Bone Formation: Molecular Clones and Activites", Science, (Dec. 1988), vol. 242, pp. 1528–1534.

Wrana, J. L., T. Kubota, Q. Zhang, C. M. Overall, J. E. Aubin, W. T. Butler and J. Sodek, "Regulation of Transformation-sensitive Secreted Phosphoprotein (SPPI/osteopontin) Expression by Transforming Growth Factor-$\beta$", Biochem. J., (1991), vol. 273, pp. 523–531.

"Bone-inducing agent (BIA) from cultured human Saos-2 osteosarcoma cells", Anderson, H. C., K. Sugamoto, D. C. Morris, H. H. T. Hsu, & T. Hunt, Bone and Mineral, 16 (1992) pp. 49–62.

"Oncogene, Tumor Suppressor Gene, and Growth Signal Transduction Alterations in a Series of Chemically-Induced Rat Osteosarcomas", Isfort, R. J., D. C. Cody, G. Lovell, & C. J. Doersen, Poster Presentation, Seventh Annual Oncogene Meeting, Frederick, Md., Jun. 24, 1991.

"Growth Factors in Development, Transformation, and Tumorigenesis", Cross, M. and T. M. Dexter, Cell, vol. 64, pp. 271–280, (1991).

"Insulin Promotes Growth of the Cultured Rat Osteosarcoma Cell Line UMR-106-01:An Osteoblast-Like Cell", Hickman, J. and A. McElduff, Endocrinology, vol. 124, No. 2, pp. 701–706, (1989).

"Negative regulators of cell growth", Wang, J. L. and Y. M. Hsu, TIBS 11 (1986).

"Growth Factors: Mechanism of Action and Relation to Oncogenes", Heldin, C. H. and Westermark, B., Cell, vol. 37, pp. 9–20, (1984).

"Production of An Insulin-like Growth Factor by Osteosarcoma", Blatt, J., C. White, S. Dienes, H. Friedman and T. P. Foley, Jr., Biochemical and Biophysical Research Communications, vol. 123, No. 1, pp. 373–376, (1984).

RAT OSTEOSARCOMA CELL LINE OSR-8

TECHNICAL FIELD

This invention relates generally to a novel cell line, and specifically to a novel rat osteosarcoma cell line, as well as to certain growth factors produced by the cell line.

BACKGROUND OF THE INVENTION

Polypeptide growth factors play a key role in regulating the development of multicellular organisms and in the processes of tissue maintenance and repair. (Cross and Dexter (1991) *Cell*, Vol. 64, pp. 271–280; Aaronson (1991) *Science*, Vol. 254, pp. 1146–1153.) At the cellular level, growth factors are involved in regulating proliferation and the progressive acquisition of the differentiated phenotype. Growth factors are capable of stimulating cellular proliferation as well as inhibiting cellular proliferation and many growth factors have been found to be multifunctional (Sporn and Roberts (1988) *Nature*, Vol. 332, pp. 217–219). The highly coordinated functions of growth factors is perhaps best exemplified in the development of the hematopoiectic cell system (Metcalf (1989) *Nature*, Vol. 339, pp. 27–30) where a limited number of stem cells give rise to a larger population of developmentally restricted progenitor cells. These progenitors cells are further stimulated to proliferate and differentiate into mature lymphoid, erythroid and myeloid cells. A balance between cell types and numbers of cells must be maintained throughout the developmental cascade. This requires the concerted actions of growth factors which commit a cell (now developmentally restricted) along a particular cell lineage, of growth factors which stimulate the proliferation of committed cells, and finally, of growth factors which promote the differentiation of the committed cells and inhibit the proliferation of the mature, fully differentiated cells.

Tumor cells represent naturally occurring examples of cells where the processes that control cellular proliferation and differentiation have been uncoupled (Cross and Dexter (1991) *Cell*, Vol. 64, pp. 271–280; Aaronson (1991) *Science*, Vol. 254, pp. 1146–1153). The observation that many types of tumor cells secrete growth factors suggests that these factors can contribute to the tumorigenic process as well as normal cellular processes. Tumor cells have been found to secrete autocrine growth factors which stimulate the proliferation of the tumor cells themselves and paracrine growth factors which stimulate surrounding cells to secrete factors promoting the proliferation of the tumor cells. Paracrine factors can also stimulate the surrounding cells to provide a cellular environment promoting the survival of the tumor cells. For example, many types of tumor cells secrete growth factors that recruit endothelial cells and stimulate their proliferation and differentiation resulting in a new vasculature supplying nutrients for the tumor cells (Liotta et al., (1991) *Cell*, Vol. 64, pp. 327–336).

OBJECTS OF THE PRESENT INVENTION

It is an object of the present invention to provide a novel cell line.

It is also an object of the present invention to provide novel growth factors having the characteristics of growth factors produced by the cell line.

It is also an object of the present invention to provide a process for producing novel growth factors from the novel cell line.

SUMMARY OF THE INVENTION

Figure 1A:
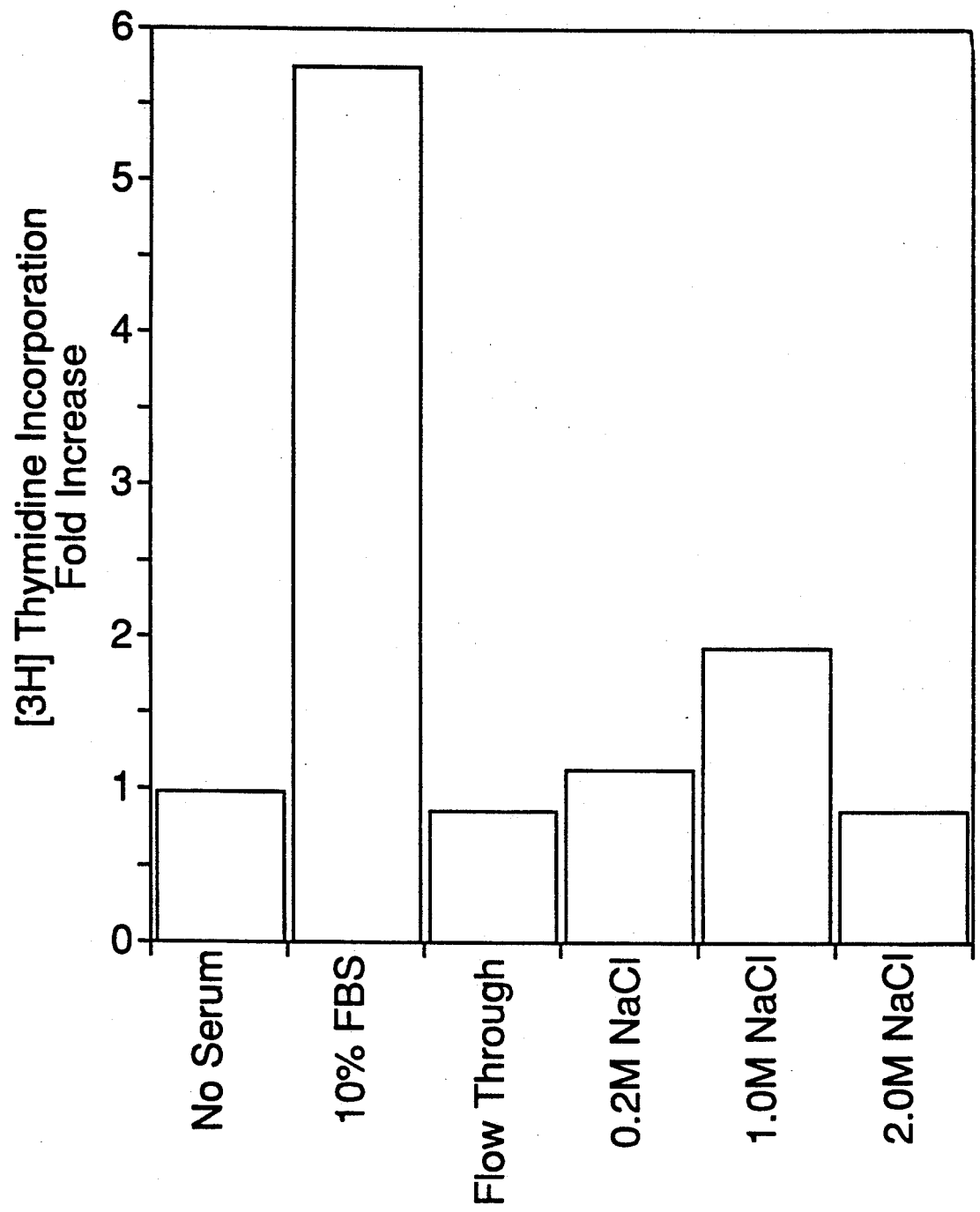
FIG. 1a: Indicates mitogenic response of OSR-2 cells to heparin agarose fractionated conditioned medium from OSR-8 cells.

The present invention relates to a novel cell line isolated from a rat osteosarcoma wherein the cell line has the following characteristics: a) a normal p53 gene; b) a normal RB-1 gene; c) a normal c-myc gene; d) a normal c-fos gene; e) a deregulated immediate early gene response; f) a canalicular network MATRIGEL TM growth pattern; g) poorly tumorigenic in congenitally athymic mice; h) no alkaline phosphatase activity; i) an ability to produce one or more of the following growth factors: 1) a non-heparin binding growth factor, 2) a first heparin binding growth factor, 3) a second heparin binding growth factor, and 4) a third heparin binding growth factor; and j) an ability to be serially propagated greater than sixty population doublings.

The present invention also relates to growth factors having the characteristics of growth factors isolated from the rat osteosarcoma cell line.

The present invention further relates to a process for producing such growth factors comprising growing the cells of the present invention in a culture medium and recovering the growth factors.

DETAILED DESCRIPTION OF THE INVENTION

As used herein, "OSR-8" refers to the novel cell line of the present invention, American Type Culture Collection (ATCC) Accession No. CRL 11070.

As used herein, "OSR-2" means cell line ATCC No. CRL 11065.

As used herein, "w/v" and "v/v" means percent by weight and percent by volume, respectively.

As used herein, "tumorigenic" means an ability to form tumors in a host animal.

As used herein, "heparin agarose elution property of XM NaCl" means the molarity of NaCl used to achieve elution of a protein from a heparin agarose column when a conditioned media comprising the protein is subjected to the heparin agarose column procedure described below, wherein X is a numerical value.

The present invention relates to a novel cell line isolated from a rat osteosarcoma wherein the cell line has the following characteristics: a) a normal p53 gene; b) a normal RB-1 gene; c) a normal c-myc gene; d) a normal c-fos gene; e) a deregulated immediate early gene response; f) a canalicular network MATRIGEL TM growth pattern; g) poorly tumorigenic in congenitally athymic mice; h) no alkaline phosphatase activity; i) an ability to produce one or more of the following growth factors: 1) a non-heparin binding growth factor, 2) a first heparin binding growth factor, 3) a second heparin binding growth factor, and 4) a third heparin binding growth factor; and j) an ability to be serially propagated greater than sixty population doublings.

Preferably, the non-heparin binding growth factor has an inability to bind heparin and an ability to stimulate NIH-3T3 cells.

Preferably, the first heparin binding growth factor has a heparin agarose elution property of from about 0 to about 0.2M NaCl, more preferably from greater than 0 to less than or equal to 0.2M NACL, and has an ability to stimulate NIH-3T3 cells.

Preferably, the second heparin binding growth factor has a heparin agarose elution property of from about 0.2 to about 1.0M NaCl, more preferably from greater than 0.2 to less than or equal to 1M NaCl, an ability to stimulate OSR-2 cells, and an ability to stimulate MC3T3-E1 cells.

Preferably, the third heparin binding protein has a heparin agarose elution property of from about 1.0 to about 2.0M NaCl, more preferably from greater than 1.0 to about 2.0M NaCl, and an ability to stimulate MC3T3-E1 cells.

Preferably, the cell line has the characteristics of American Type Culture Collection Accession No. CRL 11070.

The present invention further relates to growth factors having the characteristics of the above-identified growth factors.

Preferably the growth factor is isolated from a cell line having the characteristics of a cell line of the present invention.

The present invention further relates to a process for producing such growth factors comprising growing the cells of the present invention in a culture medium and recovering the growth factors.

An alternative way of obtaining the growth factors produced by the cell line of the present invention is by isolation of the growth factor mRNA for use by those skilled in the art for expression of the protein of interest. Protein expression from mRNA covers a wide variety of techniques including PCR methodologies using a number of organisms for the final expression of the protein including bacteria, fungus, animal cells, insect cells and plant cells as well as noncellular protein expression methodologies (for an overall review of molecular biology techniques used in protein expression cloning see Sambrook et al. (1989) *Molecular Cloning—A Laboratory Manual*, 2nd edition, Cold Spring Harbor Laboratory Press, Cold Spring Harbor, N.Y.). Briefly, this procedure involves isolating mRNA from an osteosarcoma cell line which codes for the growth factor, making cDNA of the mRNA, cloning the cDNA into an expression vector, expressing the cDNA in a host, and recovering a recombinant form of the growth factor. More preferably, this procedure involves isolation of mRNA from the osteosarcoma cell, making cDNA from the mRNA, cloning of the cDNA into an appropriate expression source, expression of the protein of interest from the cDNA inserted into the expression vector, screening the expression source for the protein of interest, purifying the expression clone containing the cDNA coding for the protein of interest, and expression of this purified cDNA in an expression vector in an appropriate expression source for large scale synthesis of the protein of interest. Multiple technical variations of this general expression schemes are well understood by those skilled in the art and all would apply.

The cell line of the present invention is useful as a biological source for the growth factors of the present invention and/or the mRNA coding for such growth factors. The growth factors of the present invention are useful for one or more of the following: 1) treating diseases affecting the bone and cartilage (e.g. those growth factors demonstrating an ability to stimulate osteoblast cells), and/or 2) wound healing (e.g., those growth factors demonstrating an ability to stimulate fibroblast cells).

STATEMENT OF DEPOSIT

OSR-8 has been deposited at the American Type Culture Collection, 12301 Parklawn Drive, Rockville, Md. 20852, U.S.A., on Jun. 5, 1992. The deposited strain has been assigned Accession No. CRL 11070.

The subject cultures have been deposited under conditions that assure access to the cultures will be available during the pendency of this patent application to one determined by the Commissioner of Patents and Trademarks to be entitled thereto under 37 CFR §1.14 and 35 USC §122. The deposits are available as required by foreign patent laws in countries wherein counterparts of the subject application, or its progeny, are filed. However, it should be understood that Applicants' granting of permission to the depository to distribute samples of the deposit does not constitute an express or implied license to practice the invention claimed in any patent issuing on the subject application or any other patent.

The subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least thirty (30) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

ESTABLISHMENT OF THE OSR-8 CELL LINE

A cell line, OSR-8, was established from a tumor excised from a Sprague-Dawley rat with osteosarcoma. The site of the excised tissue was the right tibia. The tumor tissue was aseptically remove from the euthanized animal and carefully trimmed of connective tissues. The tumor was minced in a culture dish (100 mm diameter) containing 15 ml of growth medium (10% fetal bovine serum, 90% RPMI 1640 medium (GIBCO)) further supplemented with penicillin (100 units/ml, GIBCO), Fungizone (0.25 microgram/ml, GIBCO) and streptomycin (100 micrograms/ml,GIBCO), and incubated at 37° C. in an atmosphere of 5% $CO_2$ and 95% air with a relative humidity of approximately 95%. The adherent cells which migrated from the minced tumor pieces onto the surface of the culture dish were further expanded as a cell population using standard tissue culture techniques. Once the OSR-8 cell line reached confluence in a tissue culture flask (150 $cm^2$ surface area), the cell line was designated as having a mean population doubling of 1. At this stage, the cells were subcultured in growth medium (10% fetal bovine serum, 90% RPMI 1640 medium) with no antibiotic or antimycotic supplements. The OSR-8 cell line was routinely tested for mycoplasma contamination by DAPI assay (Stanbridge (1981) *Isr. J. Med. Sci.*, Vol. 17, pp. 563-568) and was found to be negative.

The OSR-8 cell line was found to be poorly tumorigenic when assayed for tumor formation in congenitally athymic (nu/nu) mice (Harlan Sragueu Dawley, Inc.). OSR-8 cells at a mean population doublings of 7 and 14, were injected subcutaneously in the mid-flank region of the animals at an innoculum of approximately $1 \times 10^7$ cells per site. For each population doubling, a total of eight sites (two per animal) were injected. Only one tumor arose at the site of injection with a latent period of approximately eleven months.

CHARACTERISTICS OF THE OSR-8 CELL LINE

The OSR-8 cell line can be serially propagated in culture with no known limited life span. The OSR-8 cell line displays a limited, immature osteoblast-like phenotype in vitro. The cells show no staining for the presence of alkaline phosphatase (Rodan and Rodan (1983) *Bone and Mineral Research*, Annual 2 (Peck, ed.) pp. 244-285) as detected by a cytochemical assay (Sigma Chemical Company, Procedure 85). It has been reported (Vukicevic et al., (1990) *Cell*, Vol. 63, pp. 437-445) that osteoblastic cells are capable of forming cell clusters exhibiting networks of canalicular cell processes when cultured on reconstituted basement membrane extracts such as MATRIGEL™ a solubilized basement membrane available from (Collaborative Biomedical Products, Bedford, Md.) containing laminin, collagen type IV, heparin sulfate, proteoglycan and entactin). Fibroblasts, chondrocytes and embryonic stem cells did not demonstrate the canalicular cell processes. OSR-8 cells when cultured on MATRIGEL at a density of approximately 50,000 cells per well of a standard 24-well tissue culture plate formed many clusters of cells with a network of canalicular cell processes. This growth pattern was very similar to the cell clusters with the characteristic canalicular processes that were formed by the osteoblastic MC3T3-El cells plated at an equivalent density (Sudo et al ., (1983) *J. Cell Biol.* Vol. 96, pp. 191-198; Vukicevic et al., (1990) *Cell*, Vol. 63, pp. 437-445).

MOLECULAR CHARACTERIZATION OF THE OSR-8 CELL LINE

In order to characterize the OSR-8 cell line in terms of unique mutations which can identify this cell line we have screened the cell line for mutations in genes which are commonly mutated in osteosarcomas. This molecular fingerprint of the OSR-8 cell provides a convenient and useful way to identify this cell line because these mutations are critical for the growth of these cells and is not expected to change.

In this respect human osteosarcomas have been extensively studied with respect to mutations in the retinoblastoma (RB-1) and p53 tumor suppressor genes (Iavarone et al., (1992) *Proc. Natl. Acad. Sci. USA*, Vol. 89, pp. 4207-4209; Diller et al., (1990) *Mol. Cell. Biol.*, Vol. 10, pp. 5772-5781; Masuda et al., (1987) *Proc. Natl. Acad. Sci. USA*, Vol. 84, pp. 7716-7719; Levine and Momand (1990) *Biochem. et Byophys. Acta*, Vol. 1032, pp. 119-136; Miller et al., (1990) *Cancer Res.* Vol. 50, pp. 7950-7954; Friend et al., (1987) *Proc. Natl. Acad. Sci. USA*, Vol . 84, pp. 9059-9063; Mulligan et al., (1990) *Proc. Natl. Acad. Sci. USA* Vol. 87, pp. 5863-5867; Hansen et al., (1985) *Proc. Natl. Acad. Sci. USA*, Vol. 82, pp. 6216-6220; Horowitz et al., (1989) *Science*, Vol. 243, pp. 937-940; Toguchida et al., (1989) *Nature*, Vol. 338, pp. 156-158). RB-1 mutations include point mutations, deletions, and splicing mutations (Friend et al., (1987) *Proc. Natl. Acad. Sci. USA*, Vol. 84, pp. 9059-9063; Levine and Momand, (1990) *Biochem. et Biophys. Acta*, Vol. 1032, pp. 119-136; Mori et al., (1990) *Oncogene* Vol. 5, pp. 1713-1717; Horowitz et al ., (1989) *Science*, Vol. 243, pp. 937-940). All of these mutations result in the production of a non-functional RB-1 protein. RB-1 is believed to function by acting as a "brake" on cellular proliferation at the appropriate time in the cell cycle. Control of the RB-1 function is achieved by selective and timely phosphorylation of RB-1 protein; phosphorylated RB-1 allows cellular proliferation while unphosphorylated RB-1 protein inhibits cellular proliferation (Laiho et al., (1990) *Cell*, Vol. 62, pp. 175-185; DeCaprio et al., (1989) *Cell*, Vol. 58, pp. 1085-1095; Buchkovich et al., (1989) *Cell*, Vol. 58, pp. 1097-1105; Chen et al., (1989) *Cell*, Vol. 58, pp. 1193-1198; Furukawa et al., (1990) *Proc. Natl. Acad. Sci. USA*, Vol . 87, pp. 2770-2774). RB-1 control of cellular proliferation is one part of a closely regulated network of cell cycle controls, which include the cell cycle control proteins c-myc, c-fos and TGF-B (Laiho et al., (1990) *Cell*, Vol. 62, pp. 175-185; Moses et al., (1990) *Cell*, Vol. 63, pp. 245-247; Robbins et al., (1990) *Nature*, Vol. 346, pp. 668-671).

The p53 tumor suppressor gene was originally identified as an SV40 large T antigen binding protein whose expression was greatly increased (approximately 5-100 fold at the protein level) during SV40 cellular transformation (Levine and Momand, (1990) *Biochem. et Biophys. Acta*, Vol. 1032, pp. 119-136; Levine et al., (1991) *Nature*, Vol. 351, pp. 453-456). The p53 gene has since been found to be mutated in a variety of tumor types (Hollstein et al., (1991) *Science*, Vol. 253, pp. 49-53) including human osteosarcoma cells (Mulligan et al., (1990) *Proc. Natl. Acad. Sci. USA*, Vol. 87, pp. 5863-5867; Miller et al., (1990) *Cancer Res.*, Vol. 50, pp. 7950-7954; Masuda et al., (1987) *Proc. Natl. Acad. Sci. USA*, Vol. 84, pp. 7716-7719; Diller et al., (1990) *Mol. Cell. Biol.*, Vol. 10, pp. 5772-5781). Mutation of the p53 gene either results in an altered protein which does not function normally or a complete loss of protein. Both of these mechanisms result in the absence of a functional p53 protein (Halevy et al., (1990) *Science*, Vol 250, pp. 113-116; Chen et al., (1990) *Science*, Vol. 250, pp. 1576-1580; Milner and Medcalf, (1991) *Cell*, Vol. 65, pp. 765-774) and cellular transformation. The p53 protein is believed to function in several ways. The p53 protein is a transcriptional activator since p53 protein binds to specific DNA sequences (Raycroft et al., (1990) *Science*, Vol. 249, pp. 1049-1051; Kern et al., (1991) *Science*, Vol. 252, pp. 1708-1711) and contains an NH$_2$-terminal acidic domain which efficiently activates the transcription of genes in both yeast and mammalian cells (Fields and Jang, (1990) *Science*, Vol. 249, pp. 1046-1049). The protein produced from mutated p53 genes does not transcriptionally activate responsive genes (Raycroft et al., (1990) *Science*, Vol. 249, pp. 1049-1051). In addition, p53 regulates DNA replication since wild-type protein but not protein from mutated p53 genes associates with replication complexes (Levine et al., (1991) *Nature* Vol. 351, pp. 453-456; Levine and Momand, (1990) *Biochem. et Biophys. Acta* Vol. 1032, pp. 119-136) and is phosphorylated by p34(cdc2)-p60 and p34(cdc2)-cyclin B complexes (Bischoff et al., (1990) *Proc. Natl. Acad. Sci. USA*, Vol. 87, pp. 4766-4770; Milner et al., (1990) *EMBO J*, Vol. 9, pp. 2885-2889).

Two additional transforming genes which have been implicated in human and non-human osteosarcoma formation are the fos and myc oncogenes. The oncogenic variant of c-fos, v-fos, was first isolated as the transforming gene in retroviruses which resulted in murine osteosarcoma formation (Varmus (1984) *Ann. Rev. Genet.*, Vol. 18, pp. 553-612). Interestingly, transgenic mice carrying the v-fos oncogene display both cartilage and osteosarcoma tumors (Wang et al., (1991) *EMBO J*, Vol. 10, pp. 2437-2450). Oncogenic mutation of c-fos results when the fos gene is either over expressed or inappropriately expressed as a result of either viral transduction or mutation. C-fos functions in the cell, in conjunction with c-jun as the complex which binds the AP-1 transcriptional activation site (Abate et al., (1990) *Science*, Vol. 249, pp. 1157-1161; Sassone-Corsi et al., (1988) *Cold Spring Harbor Symposia on Quantative Biology* LIII, 749-760).

C-myc has been found to be mutated both in radiation induced murine osteosarcomas (Sturm et al., (1990) *Cancer Res.*, Vol. 50, pp. 4146-4153) and in primary human osteosarcoma tumors (Bogenmann et al., (1987) *Cancer Res.*, Vol. 47, pp. 3808-3814). The myc oncogene was originally identified as the transforming gene in several retroviruses (v-myc) and c-myc mutations in a variety of tumor types were later identified (DePinho et al., (1987) *J. Cell Biochem.*, Vol. 33, pp. 257-266; Varmus (1984) *Ann. Rev. Genet.*, Vol. 18, pp. 553-612). C-myc is most commonly amplified or translocated, both of which, along with retroviral transduction, result in the inappropriate expression of the myc gene (Varmus (1984) *Ann. Rev. Genet.*, Vol. 18, pp. 553-612; DePinho et al., (1987) *J. Cell Biochem*, Vol. 33, pp. 257-266). Myc protein and the Max protein form a complex which binds the regulatory region of genes, via a unique sequence, to control their expression (Blackwood and Eisenman, (1991) *Science*, Vol. 251, pp. 1211-1217; Cole (1991) *Cell*, Vol. 65, 715-716). C-myc, along with c-fos are immediate early genes and are believed to play a central role in mitogenic signalling in the cell (Rozengurt (1986) *Science*, Vol. 234, pp. 161-166).

An additional way to assay c-fos and c-myc functional activity is to determine if theses genes are transcriptionally activated following mitogenic stimulation. C-fos and c-myc are both members of a class of genes called the immediate early genes (Sassone-Corsi et al., (1988) *Cold Spring Harbor Symposia on Quantitative Biology* LIII, 749-760; Depinho et al., (1987) *J. Cell Biochem.*, Vol. 33, pp. 257-266). Genes in this class are transcriptionally activated following mitogenic stimuli usually within 1 hour and without the need of protein synthesis (Almendral et al., (1988) *Mol. Cell. Biol.*, Vol. 8, pp. 2140-2148; Greenberg et al., (1986) *Mol. Cell. Biol.*, Vol. 6, pp. 1050-1057). Since this is a complex pathway, alterations in immediate early gene transcription is indicative of either a mutation in the cellular pathway which leads from the receptor/plasma membrane to the gene/nucleus of the cell or a mutation which leads to the autocrine expression of a growth factor. Either of the above mutated phenotypes lead to a down regulation and subsequent inhibition of expression of the c-myc and c-fos genes following serum starvation and mitogen stimulation.

CHARACTERIZATION OF TUMOR SUPPRESSOR GENES AND ONCOGENES

High molecular weight DNA was isolated from the OSR-8 cell line as follows. Approximately $1 \times 10^8$ cells were cultured as described above until confluent. These cells were then scraped off the tissue culture flask into culture media, collected by centrifugation at 3300 g for 5 minutes, the culture media was removed from the cell pellet and the pellet was resuspended in 9.5 ml of NET buffer (100 mM sodium chloride, 10 mM Tris—pH 8.0, 1 mM EDTA). To the resuspended DNA was added 50 ul of 10 mg/ml of proteinase K (Boehringer Mannheim) and 0.5 ml of 10% (W/V) sodium dodecyl sulphate/water. This mixture was mixed well and incubated at 55° C. for one hour followed by extraction twice with an equal volume of a 50:50 mixture of phenol:chloroform. The aqueous phase was collected by centrifugation at 3300 g for 5 minutes and re-extracted with an equal volume of chloroform. The aqueous phase was collected by centrifugation at 3300 g for 5 minutes, removed to a new tube and to it was added 1 ml of 3M sodium acetate pH 5.2 and 20 ml of 100% ethanol. This solution was mixed well and incubated at $-20°$ C. for 2 hours followed by the collection of high molecular weight DNA by centrifugation at 3300 g for 30 minutes. The high molecular weight DNA was washed once with 5 ml of 70% ethanol/water (v/v), dried and resuspended in TE (10 mM Tris-pH 8.0 and 1 mM EDTA) at a concentration of 1 mg/ml.

For restriction enzyme analysis, 20 ug of the above isolated high molecular weight DNA in 20 ul TE was added to 2.5 ul of 10X restriction enzyme buffer (1X restriction enzyme buffer consist of 50 mM Tris—pH 8.0, 10 mM magnesium chloride, and 100 mM sodium chloride) and 2 ul of restriction enzyme (either Eco RI or Hind III at 10 units/ml both from New England Biolabs) and this mixture was incubated at 37° C. for 16 hours. Following incubation, the above solution was added to 3 ul of 10X gel loading buffer (10X gel loading buffer is 0.25% bromophenol blue, 0.25% xylene cyanol, 25% Ficoll type 400, 10 mM EDTA in water) and the restriction endonuclease generated fragments were separated by agarose gel electrophoresis. Agarose gel electrophoresis was performed as follows. A 0.6% (w/v) agarose (Bethesda Research Laboratories) gel in 1X TBE (1X TBE consist of 0.089 M Tris, 0.089 M boric acid, and 0.002 M EDTA) was poured in a BioRad horizontal gel electrophoresis apparatus, the above DNA solution was loaded into a well and electrophoresis was performed in a 1X TBE solution for 16 hours at 20 volts. Following electrophoresis, the gel was stained for 1 hour in 0.5 ug/ml ethidium bromide (Sigma Chemical Company)/water solution followed by photography under 302 nm ultraviolet light irradiation. The gel was then prepared for Southern blotting as follows. The gel was soaked for 1 hour in a solution of 1.5M sodium chloride and 0.5M sodium hydroxide with constant shaking followed by an incubation for 1 hour in a solution of 1.5M sodium chloride and 1M Tris—pH 8.0 with constant shaking. The gel was then transferred to an LKB VacuBlot apparatus (LKB Scientific) prefitted with a sheet of BAS-NC nitrocellulose (Schleiser and Schuel) and the transfer of DNA from the agarose gel to the nitrocellulose membrane was performed under 40 cm.$H_2O$ of pressure using 10X SSC (10X SSC is 1.5M sodium chloride and 0.15M sodium citrate, pH 7.0) as the transfer medium. The OSR-8 DNA Southern blot was then used in a hybridization analysis as follows. The nitrocellulose filter was first wet in 6X SSC followed by prehybridization in hybridization buffer [50% formamide (molecular biology grade, Bethesda Research Laboratories), 5X Denhardt's solution (Denhardt's solution is 0.1% Ficoll, 0.1% polyvinylpyrrolidone, and 0.1% bovine serum albumin pentax fraction V—all from Sigma Chemical Company), 5X SSPE (20X SSPE is 3M sodium chloride, 0.2M sodium phosphate, and 0.02M EDTA —pH 7.4), 0.1% sodium dodecyl sulphate, and 100 ug/ml of denatured salmon sperm DNA (Sigma Chemical Company)] for 4 hours at 42° C. with constant agitation. Molecular probes for the tumor suppressor genes RB-1 (ATCC #57450) and p53 (Levine and Momand (1990) Biochemica et Biophysica Acta 1032, 119–136) and the oncogenes c-myc (ATCC #41008) and c-fos (ATCC #41040) were radiolabelled using an Amersham nick translation kit and [32P]dCTP (ICN) to a specific activity of $1 \times 10(8)$ cpm/ug DNA by following the manufacturers recommendations. These radiolabelled probes were then added to the hybridization solution/nitrocellulose filter of the prehybridization step and incubated at 42° C. for 40 hours with constant agitation. Following hybridization, the nitrocellulose filters (blots) were first incubated in 2X SSC and 0.1% SDS at room temperature for 1 hour followed by an incubation in 0.2X SSC and 0.1% SDS at 65° C. for 1 hour. The results of the hybridization experiment were visualized by autoradiography at −70° C. Following autoradiography, the films were developed and used in data analysis.

The molecular analysis of the OSR-8 cell line RB-1, p53, c-myc and c-fos genes indicated that all these genes appeared normal (non-mutated, wild-type) as compared to a non-tumorigenic Sprague-Dawley rat cell control at the above described level of analysis (restriction enzyme digestion and Southern blotting).

RB-1 AND D53 PROTEIN ANALYSIS

Immunological identification of the p53 and RB-1 proteins were performed as follows. $1 \times 10^6$ OSR-8 cells were labelled for 4 hours with 100 uCi/ml of [35S]methionine (TranSlabel—ICN) in methionine-free RPMI-1640 (GIBCO) media containing 10% fetal bovine serum for 4 hours at 37° C. Following labelling, the cells were scraped off the tissue culture plastic into the labelling media, the cells were collected by centrifugation at 3300 g for 5 minutes, followed by removal of the labelling media and the snap freezing of the cell pellet in liquid nitrogen. The frozen cell pellets were dissolved in 1 ml of ice-cold lysis buffer (50 mM Tris—pH 8.0, 5 mM EDTA, 150 mM sodium chloride, 0.5% Nonidet P-40, and 1 mM phenylmethylsulfonylfluoride) by vigorous vortexing and incubated on ice with intermediate vortexing for 30 minutes. The lysates were clarified of nonsoluable material by centrifugation at 10,000 g for 30 minutes, the supernate was removed to a new tube to which was added 10 ul of antibodies specific for either mutant p53 (Oncogene Science p53 Ab-3), normal and mutant p53 (Oncogene Science p53 Ab-1), or RB-1 (a 50:50 mixture of Oncogene Science RB Ab-2 and Ab-3), and 50 ul of a Protein A/G agarose (Boehringer Mannheim):lysis buffer (50:50). The above mixture was incubated overnight at 4° C. with constant shaking. The cell lysate was aspirated off and the antigen/antibody/-protein A-G pellet was washed one time in 1 ml of lysis buffer, one time in 1 ml of SNTE buffer (50 mM Tris-pH 7.4, 5 mM EDTA, 5% sucrose—w/v, 1% Nonidet P-40, and 0.5 M sodium chloride), and one time in 1 ml of RIPA buffer (50 mM Tris—pH 7.4, 150 mM sodium chloride, 1% Triton X-100, 0.1% sodium dodecyl sulphate and 1% sodium deoxycholate). Following washing, the antigen/antibody/protein A-G agarose pellet was redissolved in 25 ul of sample buffer (62.5 mM Tri-g—pH 6.8, 2% sodium dodecyl sulphate, 10% glycerol, 5% 2-mercaptoethanol), boiled at 100° C. for 2–3 minutes, and applied to a well of a 10% SDS-PAGE gel. SDS-PAGE was performed as described by Laemmli (Laemmli, U.K. (1970) Nature 227, 680–685) for 6–8 hours at 30 mA constant current per gel. Following electrophoresis, the SDS-PAGE gels were incubated in 30% methanol and 10% acetic acid for at least 1 hours, impregnated with ENHANCE (NEN-DuPont) according to the manufacturers recommendations, dried onto Whatman 3 mm paper using a BioRad gel dryer set at 60° C. for 2 hours and autoradiography at −70° C. was performed.

The results of the p53 and RB-1 protein analysis of the OSR-8 cell line indicated that both p53 and RB-1 protein were normal both in their level of expression and the protein's physical characteristics.

IMMEDIATE EARLY GENE EXPRESSION FOLLOWING MITOGEN STIMULATION

In order to characterize the immediate early gene (c-myc and c-fos) transcription following mitogen stimulation in the OSR-8 cell line the following experiments were performed. Approximately $1 \times 10^8$ cells were grown to 70% confluence in a tissue culture flask in 25 ml of standard growth media. The cells were washed 2 time with serum-free media followed by the addition of 25 ml of serum-free culture media and incubated for 12–16 hours at 37° C. under an atmosphere of 10% carbon dioxide in an incubator. To the serum-starved cells was added 3 ml (10% v/v) of fetal bovine serum and 10 ug/ml of cycloheximide and the cells were incubated as above for 3 hours. One group of cells was not mitogen stimulated and remained serum-starved. RNA from the mitogen stimulated and non-stimulated cells was isolated using the RNAzol (Cinna/Biotecx Inc.) methodology according to the manufacturer's recommendation. Briefly, $1 \times 10^8$ cells were lysed in situ with 10 ml of RNAzol, the lysate was collected, 1 ml of chloroform was added to the lysate, the samples were vortexed vigorously for 15 seconds, and the mixture was then centrifuged at 12,000 g (4° C.) for 15 minutes. The upper (aqueous) phase was transferred to a new tube, an equal volume of isopropanol was added to it, the samples were cooled to −20° C. for 45 minutes, followed by pelleting of the RNA by centrifugation at 12,000 g (4° C.) for 15 minutes. The pelleted RNA was washed once with ice-cold 70% ethanol/water, dried, and resuspended in RNAse-free water at 20 ug/4.5 ul. RNA formaldehyde agarose gel electrophoresis was performed as described (Sambrook et al., (1989) Molecular Cloning, Cold Spring Harbor Press, Cold Spring Harbor, N.Y.). Briefly, 20 ug of total cellular RNA was denatured by heating to 55° C. for 15 minutes in denaturation buffer [4.5 ul RNA solution, 2.0 ul 10X RNA gel buffer (0.2M MOPS —pH 7.0, 50 mM sodium acetate, and 10 mM EDTA), 3.5 ul formaldehyde and 10.0 ul formamide] followed by the addition of 2 ul of loading buffer (50% glycerol, I mM EDTA, 0.4% bromophenol blue, and 0.4% xylene cyanol) and loading of the sample into a well of the formaldehyde gel (1% agarose, 20 mM MOPS—pH 7.0, 5 mM sodium acetate, 1 mM EDTA and 2.2 M formaldehyde). Electrophoresis was performed at 30 volts (constant voltage) for 16 hours. Following electrophoresis the gel was stained with ethidium bromide (0.5 ug/ml in water) for 1 hour, destained in water for 1 hour, and photographed under 300 nm ultraviolet light using a Foto/Prep I (Fotodyne) transilluminator. Following photography, the gel was transferred to nitrocellulose (Schleicher & Schuell, BA-S NC) using a LKB Vacugene vacublotting apparatus operating at 50 cm·H$_2$O with a 20X SSC (3 M sodium chloride and 0.3 M sodium citrate—pH 7.0) fluid transfer medium. Following transfer, the RNA was fixed to the nitrocellulose filter by UV irradiation using a Stratalinker (Stratagene Inc.) UV crosslinker at 0.12 Joules/cm$^2$. Following RNA fixation, the Northern blots were used in probe hydridization studies following previously described procedures (Sambrook et al., (1989) Molecular Cloning, Cold Spring Harbor Press, Cold Spring Harbor, N.Y.) that were modified as follows. The probes of interest, c-fos (ATCC #41040) or c-myc (ATCC #41008) were radioactively labelled by using an Amersham nick translation kit following the manufacturer's recommendations. Briefly, 1 ug of probe DNA was incubated with 1X nick translation buffer, 50 uCi alpha [$^{32}$p]-dCTP (NEN), and polymerase mix in a total volume of 20 ul at 15° C. for 2 hours followed by the addition of 80 ul of 1X STE (100 mM sodium chloride, 10 mM Tris—pH 8.0, and 1 mM EDTA). Separation of the incorporated from non-incorporated nucleotides was achieved using a Biospin column (BioRad). Typically 1 ug of probe had a specific activity of greater than $1 \times 10^8$ dpm. Following nick translation, the probe was boiled for 10 minutes and added to a prehybridized filter (4 hours in hybridization solution at 42° C.) in 10 ml of hybridization solution [6X SSPE (3M sodium chloride, 0.2 M sodium phosphate—pH 7.4 and 20 mM EDTA), 5X Denhardt's solution (1% Ficoll, 1% polyvinyl-pyrrolidone, and 1% BSA—Pentax fraction V), 0.5% sodium dodecyl sulfate, 100 ug/ml denatured—sonicated salmon sperm DNA, and 50% formamide] and incubated for 48 hours at 42° C. Following hybridization the filters were washed at room temperature in 2X SSC -0.1% SDS followed by a wash at 65° C. with 0.2X SSC—0.1% SDS. The filters were then dried, mounted to 3MM paper (Whatman) and autoradiography at −80° C. was performed using intensifying screens (NEN).

The OSR-8 cell line displayed an altered immediate early gene response which was exemplified by an absence of transcriptional upregulation of the c-myc and c-fos gene in response to mitogen stimulation.

TABLE 1

Characterizations of the OSR-8 cell line

The OSR-8 cell line has the following characteristics;
a. a normal p53 protein/gene
b. a normal RB-1 gene/protein
C. a normal c-myc gene
d. a normal c-fos gene
e. a deregulated immediate early gene response
f. a canalicular network MATRIGEL ™ growth pattern
g. poorly tumorigenic in congenitally athymic mice
h. no alkaline phosphatase activity
i. production of a non-heparin binding growth factor
j. production of a first heparin binding growth factor
k. production of a second heparin binding growth factor
l production of a third heparin binding growth factor
m. an ability to be serially propagated greater than sixty population doublings

USE OF THE OSR-8 CELL LINE AS A SOURCE OF GROWTH FACTORS

The ability of a growth factor to stimulate, or inhibit DNA synthesis in a serum-starved quiescent cell is perhaps the most widely studied response to growth factors. This ability to stimulate, or inhibit the mitogenic response of a target cell is an indicator of the growth factor's ability to stimulate, or inhibit cellular proliferation. The mitogenic response of cells can be quantitated using a [$^3$H]thymidine incorporation assay as previously described (Isfort (1990) Somatic Cell Molec. Genet., Vol. 16, pp. 109–121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. Mitogens such as serum and various growth factors are added to the serum starved cells in a volume of 50 ul of medium, with serum-free medium serving as a control. After 16 hours incubation, the cells are exposed to 1 $\mu$Ci [$^3$H]thymidine for 6 additional hours of incubation. The cells are then harvested and lysed on glass fiber filters using a PHD cell harvester (Cambridge Technology, Inc.) and the radioactivity in the samples was assayed by scintillation spectrophotometery.

To test for the secretion of mitogenic growth factors by OSR-8 cells, serum-free conditioned medium was harvested from cell cultures. OSR-8 cells were grown to confluency in a 150 cm$^2$ tissue culture flask. The growth medium was removed and the cell monolayer was rinsed three times with approximately 15 ml of phosphate buffered saline. The cells were then incubated in 25 ml of serum free medium for approximately 24 hours, and the conditioned medium was harvested and clarified by centrifugation for 15 minutes at 2000 xg to remove cells and cellular debris. To gain some information on the types of growth factors produced by OSR-8 cells, the clarified conditioned medium was fractionated by heparin agarose chromatography (type I heparin agarose, purchased from Sigma Chemical Company). The binding properties of a variety of growth factors to heparin has been reported (Shing et al., (1984) Science, Vol. 223, pp. 1296–1298; Klagsbrun and Shing (1985) Proc. Natl. Acad. Sci. USA, Vol. 82, pp. 805–809; Hauschka et al., (1986) J. Biol. Chem., Vol. 261, pp. 12665–12674), thus allowing an empirical classification of the types of growth factors. After collecting the flow through fraction of the conditioned medium, heparin binding factors were eluted in a stepwise application of 0.2M NaCl, 1.0M NaCl, and 2.0M NaCl in 25 mM Tris buffer, pH8.0. All fractions were dialyzed versus water and lyophilized. For analysis of mitogenic activity, the lyophilized fractions were resuspended in 2.0 ml of serum free medium and sterilized by centrifugal filtration (Centrex filters, Schleicher and Schuell).

A panel of target cells was used which incorporated osteoblastic, fibroblastic and multipotential mesenchymal cell types. These include the osteoblastic cells OSR-2 (ATCC Accession No. CRL 11065) and MC3T3-E1 (Sudo et al., (1983) *J. Cell Biol.* Vol. 96, pp. 191–198); the fibroblastic cell line NIH-3T3 (American Type Culture Collection, CRL 1658); and the multipotential cell population isolated from neonatal rat muscle (designated NRM) according to slight modifications of the procedure describe by Sampath et al., (1984) *Proc. Natl. Acad. Sci. USA*, Vol. 81, pp. 3419–3423. Briefly, the tricep muscles were aseptically isolated from euthanized newborn Sprague-Dawley rats and cleaned of connective and vascular tissue. The muscles were minced and cultured in 15 ml of 10% fetal bovine serum, 90% CMRL-1066 medium (GIBCO) supplemented with antibiotics and antimycotic mixture (penicillin, 100 units/ml; streptomycin, 100 ug/ml; Fungizone, 0.25 ug/ml, GIBCO). Once the explant cultures reached confluence in a 150 $cm^2$ tissue culture flask, the (IGF-I); human recombinant insulin-like growth factor II (IGF-II); human recombinant transforming growth factor beta, type I (TGF-B1); human recombinant interleukin 1-beta (IL-IB); recombinant murine leukemia inhibitory factor (LIF); recombinant murine tumor necrosis factor alpha (TNF-a). In addition, a mixture of bone morphogenic proteins (BMP-2, BMP-3, BMP-4, and BMP-7) as isolated from bovine bone by Koenig et al., (1991) *J. Bone Mineral Res.*, Vol. 6, p. S206 was included in the analysis. The BMPs have been shown to induce the formation of cartilage and bone *in vivo* (reviewed by Wozney (1989) *Progress in Growth Factor Research*, Vol. 1, pp. 267–280) and heparin affinity chromatography was used in the purification of the bone derived BMP mixture. The results of these mitogenicity assays are summarized in Table 2.

TABLE 2

| | Mitogenesis Results Target Cell Line | | | |
|---|---|---|---|---|
| Stimulus | OSR2 (ATCC No. CRL 11065) (osteoblast) | MC3T3-E1 (osteoblast) | NRM (multipotent) | NIH-3T3 (fibroblast) |
| 0% SERUM | 0 | 0 | 0 | 0 |
| 10% SERUM | + | + | + | + |
| PDGF-AA | + | + | + | ND |
| PDGF-BB | + | + | + | ND |
| PDGF-AB | + | + | + | + |
| EGF | + | + | + | + |
| aFGF | + | + | + | + |
| bFGF | 0 | + | 0 | 0 |
| IGF-I | + | + | + | + |
| IGF-II | + | + | + | + |
| TGF-B1 | + | (−) | 0 | + |
| IL-1B | + | + | + | + |
| LIF | + | 0 | + | 0 |
| TNF-a | + | + | + | + |
| BMP2,3,4,7 | + | (−) | 0 | + |
| OSR-8 Cond. Medium | + | + | + | + |
| Heparin Agarose | | | | |
| Flow Through | 0 | 0 | ND | + |
| 0.2M NaCl | 0 | 0 | ND | + |
| 1.0M NaCl | + | + | ND | 0 |
| 2.0M NaCl | 0 | + | ND | 0 |

Table Legend. Comparison of proliferative effects of a variety of mitogens on target cells.
0 = no stimulation (equivalent to 0% serum control),
+ = mitogenic stimulation at least 50% above the 0% serum control,
− = inhibition of proliferation at least 50% of 0% serum control,
ND = not determined.

NRM cell line was designated as being at mean population doubling of 1. The NRM cell line is capable of forming multinucleate myotubes in confluent cultures and can be stimulated by TGF-BL to differentiate into chondrocyte-like cells (Seyedin et al., (1985) *Proc. Natl. Acad. Sci. USA*, Vol. 82, pp. 2267–2271).

The mitogenic responses elicited by the total conditioned serum-free medium and the heparin agarose fractionated conditioned medium from OSR-8 cells were compared to a number of known growth factors. All growth factors were purchased from GIBCO BRL, Life Technologies, Inc., and were tested over a 3–4 log concentration range incorporating the effective concentrations suggested by the supplier. The growth factors were human recombinant platelet derived growth factor-AB heterodimer (PDGF-AB); human recombinant platelet derived growth factor-AA homodimer (PDGF-AA); human recombinant platelet derived growth factor-BB homodimer (PDGF-BB); human recombinant acidic fibroblast growth factor (aFGF); human recombinant basic fibroblast growth factor (bFGF); human recombinant epidermal growth factor (EGF); human recombinant insulin-like growth factor I The results of the mitogenicity assay (Table 2) indicate that OSR-8 cells produce a number of growth factors that can be fractionated from the serum-free conditioned medium by heparin agarose chromatography. Based on the selective stimulation of the flow through, 0.2M NaCl, and 1.0M NaCl fractions, the identity of the growth factors present in these fractions is not readily apparent, as none of the known growth factors tested show a similar profile of mitogenic activity for the target cells in the panel. The mitogenic growth factors present in the flow through fraction and the 0.2M NaCl elute preferentially stimulated the proliferation of fibroblasts. The mitogenic growth factor, or growth factors, present in the 1.0M NaCl fraction preferentially stimulated the proliferation of osteoblastic cells. The mitogenic activity present in the 2.0M NaCl fraction may be attributed to a member of the FGF family of growth factors (Burgess and Maciag (1989) *Annu. Rev. Biochem*, Vol. 58, pp. 575–606), or a novel growth factor. *Growth Factors Produced by OSR-8 Cells*

A panel of target cells was used to assay for the presence of mitogenic growth factors. These include the osteoblastic cells OSR-2 (ATCC Accession No. 11065) and MC3T3-E1 (Sudo et al., (1983) *J. Cell Biol.*, Vol. 96, pp. 191-198); the fibroblastic cell line NIH-3T3 (American Type Culture Collection, CRL 1658). To test for the secretion of mitogenic growth factors by OSR-8 cells, serumfree conditioned medium was harvested from cell cultures. OSR-8 cells were grown to confluency in a 150 cm$^2$ tissue culture flask. The growth medium was removed and the cell monolayer was rinsed three times with approximately 15 ml of phosphate buffered saline. The cells were then incubated in 25 ml of serum free medium for approximately 24 hours, and the conditioned medium was harvested and clarified by centrifugation for 15 minutes at 2000 x g to remove cells and cellular debris. To gain some information on the types of growth factors produced by OSR-8 cells, 20 ml of the clarified conditioned medium was applied to a heparin agarose column (1 ml bed volume, type I heparin agarose, purchased from Sigma Chemical Company), and the column was washed with 5.0 ml of 25 mM Tris buffer, pH8.0. After collecting the flow through fraction of the conditioned medium, heparin binding factors were eluted in a stepwise manner by washing the heparin agarose column with 5.0 ml of 0.2M NaCl in 25 mM Tris buffer, pH8.0; followed by 5.0 ml of 1.0 M NaCl in 25 mM Tris buffer, pH8.0; and finally 5.0 ml of 2.0M NaCl in 25 mM Tris buffer, pH8.0. All fractions were dialyzed versus water and lyophilized. For analysis of mitogenic activity, the lyophilized fractions were resuspended in 2.0 ml of serum free medium and sterilized by centrifugal filtration (Centrex filters, Schleicher and Schuell).

Figure 1B:
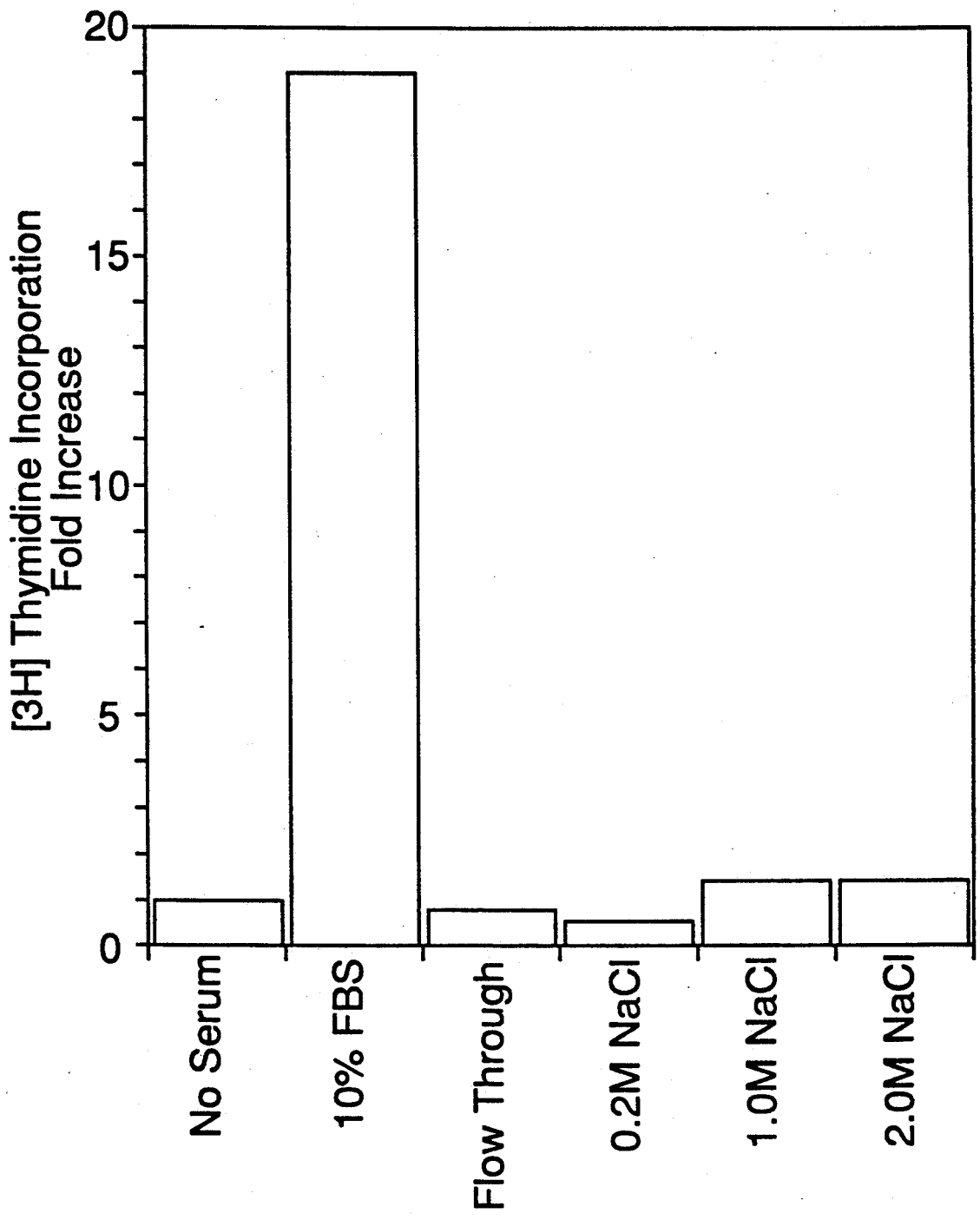
FIG. 1b: Indicates mitogenic response of MC3T3-E1 cells to heparin agarose fractionated conditioned medium from OSR-8 cells.
Figure 1C:
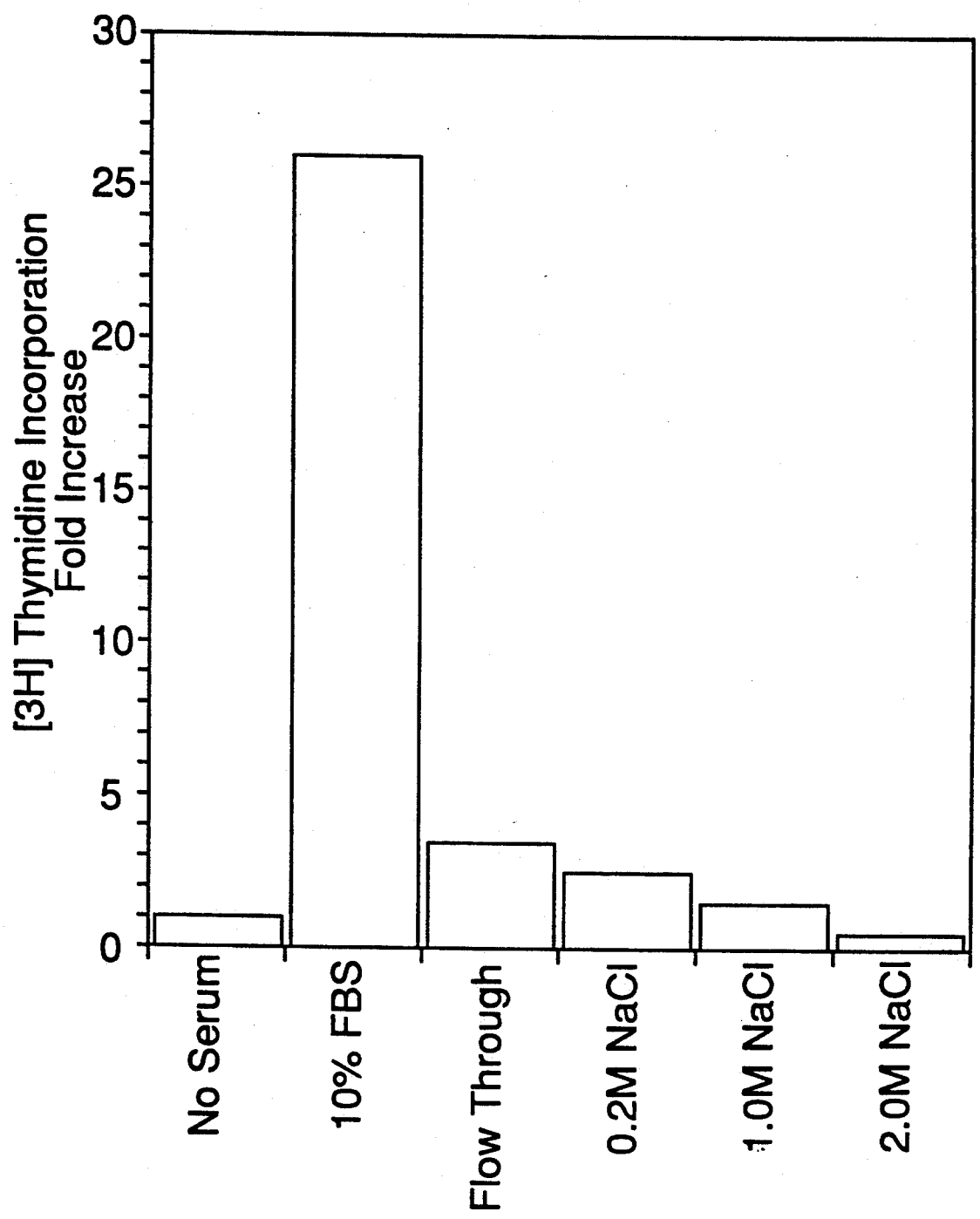
FIG. 1c: Indicates mitogenic response of NIH-3T3 cells to heparin agarose conditioned medium from OSR-8 cells.

The mitogenic response of cells was quantitated using a [$^3$H]thymidine incorporation assay as previously described (Isfort (1990) *Somatic Cell Molec. Genet.*, Vol.16, pp. 109-121). Briefly, target cells are plated at $2 \times 10^3$ cells/well in a 96 well microtiter plate and incubated overnight in growth medium to allow the cells to attach. The growth medium is removed and the cells are washed three times with phosphate buffered saline (GIBCO) followed by an 8 hour incubation in 50 ul/well of serum-free medium. The heparin agarose fractions were added to the serum starved cells in a volume of 50 ul of medium, with serum-free medium serving as a control and 20% FBS (10% FBS final concentration) serving as a positive mitogenic control. After 16 hours incubation, 10 ul of serum-free medium containing I uCi of- [$^3$H]thymidine (Amersham, 5 Ci/mmol, 185 MBq/mmol) were added to each well and the cells were incubated for 6 additional hours. The cells were then harvested and lysed on glass fiber filters using a PHD cell harvester (Cambridge Technology, Inc.) and the radioactivity in the samples was assayed by scintillation spectrophotometery. The data were calculated from the mean dpms of quadruplicate samples of the experimental groups and expressed as the fold incorporation relative to the serum-free treated cells. The mitogenic response of OSR-2 cells is shown in FIG. 1a. The mitogenic response of MC3T3-E1 cells is shown in FIG. 1b. The mitogenic response of NIH-3T3 cells is shown in FIG. 1c.

TABLE 3

Summary of Growth Factors Secreted by OSR-8 Cells

1. A non-heparin binding growth factor that preferentially stimulates fibroblasts and multipotent cells of mesenchymal origin.
2. A first heparin binding growth factor present in the 0-0.2M NaCl eluate that stimulates fibroblasts and preferentially stimulates some osteoblastic cells.
3. A second heparin binding, osteoblast specific growth factor present in the 0.2-1.0M NaCl eluate from heparin agarose chromatography that preferentially stimulates osteoblastic cells.
4. A third heparin binding growth factor present in the 1.0-2.0 M NaCl eluate that stimulates osteoblastic cells and fibroblasts which may be a member of the FGF family of growth factors.

The invention has been described herein with reference to certain preferred embodiments and examples. Obvious variations may appear to those skilled in the art. Therefore, the invention is not to be considered limited thereto but only by the claims which follow.

What is claimed is:

1. A cell line having all of the identifying characteristics of American Type Culture Collection Accession No. CRL 11070.

* * * * *

UNITED STATES PATENT AND TRADEMARK OFFICE
CERTIFICATE OF CORRECTION

PATENT NO. : 5,286,643

DATED : February 15, 1994

INVENTOR(S) : R.J.W. Doersen and R.J. Isfort

It is certified that error appears in the above-identified patent and that said Letters Patent is hereby corrected as shown below:

Column 3, line 9, "NACL" should read -- NaCL --.

Column 8, line 36, "RI" should read -- R1 --.

Column 9, line 38, "D53" should read --p53--.

Column 10, line 6, "Trig" should read --Tris--.

Column 13, line 49, "BL" should read --B1--.

Column 14, line 17, "Mitoqenesis" should read --Mitogenesis--.

Column 15, line 8, "serumfree" should read --serum-free--.

Signed and Sealed this

Eleventh Day of April, 1995

Attest:

BRUCE LEHMAN

Attesting Officer     Commissioner of Patents and Trademarks